(12) United States Patent
Jain

(10) Patent No.: US 11,007,188 B2
(45) Date of Patent: *May 18, 2021

(54) CRENOLANIB FOR TREATING FLT3 MUTATED PROLIFERATIVE DISORDERS

(71) Applicant: Arog Pharmaceuticals, Inc., Dallas, TX (US)

(72) Inventor: Vinay K. Jain, Dallas, TX (US)

(73) Assignee: AROG PHARMACEUTICALS, INC., Dallas, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/282,716

(22) Filed: Feb. 22, 2019

(65) Prior Publication Data

US 2019/0183879 A1 Jun. 20, 2019

Related U.S. Application Data

(63) Continuation of application No. 15/715,274, filed on Sep. 26, 2017, now Pat. No. 10,213,423, which is a continuation of application No. 15/195,297, filed on Jun. 28, 2016, now Pat. No. 9,801,870, which is a continuation of application No. 14/703,500, filed on May 4, 2015, now Pat. No. 9,393,240, which is a continuation of application No. 14/053,011, filed on Oct. 14, 2013, now Pat. No. 9,101,624.

(60) Provisional application No. 61/749,695, filed on Jan. 7, 2013.

(51) Int. Cl.
*A61K 9/00* (2006.01)
*A61K 45/06* (2006.01)
*G01N 33/574* (2006.01)
*A61K 31/4709* (2006.01)

(52) U.S. Cl.
CPC ........ *A61K 31/4709* (2013.01); *A61K 9/0053* (2013.01); *A61K 45/06* (2013.01); *C12Y 207/10001* (2013.01); *G01N 33/57426* (2013.01); *G01N 2333/91205* (2013.01)

(58) Field of Classification Search
CPC ...... A61K 31/4709; A61K 9/00; A61K 45/06; G01N 33/574
See application file for complete search history.

(56) References Cited

U.S. PATENT DOCUMENTS

| | | | |
|---|---|---|---|
| 5,990,146 A | 11/1999 | Boschellie et al. | |
| 7,071,337 B2 | 7/2006 | Kath et al. | |
| 7,183,414 B2 | 2/2007 | Tom et al. | |
| 9,023,880 B2 | 5/2015 | Jain | |
| 9,101,624 B2 | 8/2015 | Jain | |
| 9,393,240 B2 | 7/2016 | Jain | |
| 9,480,683 B2 | 11/2016 | Jain | |
| 9,801,869 B2 | 10/2017 | Jain | |
| 9,801,870 B2 | 10/2017 | Jain | |
| 10,213,423 B2 | 2/2019 | Jain | |
| 2004/0049032 A1 | 3/2004 | Charrier et al. | |
| 2014/0088143 A1 | 3/2014 | Jain | |
| 2014/0194464 A1 | 7/2014 | Jain | |
| 2015/0202197 A1 | 7/2015 | Jain | |
| 2015/0238479 A1 | 8/2015 | Jain | |
| 2016/0303109 A1 | 10/2016 | Jain | |
| 2018/0055834 A1 | 3/2018 | Jain | |

FOREIGN PATENT DOCUMENTS

| | | |
|---|---|---|
| EP | 2941251 | 7/2014 |
| WO | 1999016755 | 4/1999 |
| WO | 2001040217 A1 | 6/2001 |
| WO | 2002032861 A2 | 4/2002 |
| WO | 2002092599 A1 | 11/2002 |
| WO | 2003024931 A1 | 3/2003 |
| WO | 2003024969 A1 | 3/2003 |
| WO | 2003099771 A2 | 4/2003 |
| WO | 2003035009 A2 | 5/2003 |

(Continued)

OTHER PUBLICATIONS

Abu-Duhier, et al. "FLT3 internal tandem duplication mutations in adult acute myeloid leukemia define a high risk group" British Journal of Haematology. Jun. 7, 2000;111:190-195.

(Continued)

*Primary Examiner* — Shirley V Gembeh

(74) *Attorney, Agent, or Firm* — Edwin S. Flores; Daniel J. Chalker; Chalker Flores, LLP

(57) ABSTRACT

The present invention relates to the use of crenolanib, in a pharmaceutically acceptable salt form for the treatment of FLT3 mutated proliferative disorders driven by constitutively activated mutant FLT3, and to a method of treatment of warm-blooded animals, preferably humans, in which a therapeutically effective dose of crenolanib is administered to an animal suffering from said disease or condition:

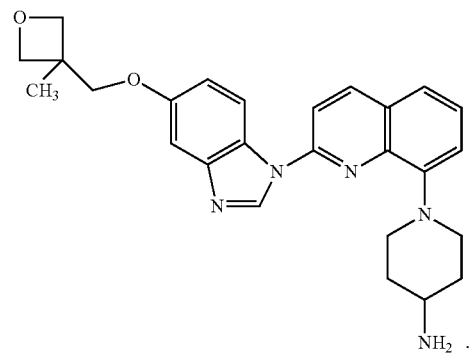

28 Claims, No Drawings

(56) References Cited

FOREIGN PATENT DOCUMENTS

| | | |
|---|---|---|
| WO | 2003037347 A1 | 5/2003 |
| WO | 2003057690 A1 | 7/2003 |
| WO | 2004005281 A1 | 1/2004 |
| WO | 2004016597 A2 | 2/2004 |
| WO | 2004018419 A2 | 3/2004 |
| WO | 2004020431 A2 | 3/2004 |
| WO | 2004039782 A1 | 5/2004 |
| WO | 2004043389 A2 | 5/2004 |
| WO | 2004046120 A2 | 7/2004 |
| WO | 2004058749 A1 | 7/2004 |
| WO | 2014107209 A2 | 7/2014 |

OTHER PUBLICATIONS

Amin, et al. "Having a higher blast percentage in circulation than bone marrow: clinical implications in myelodysplastic syndrome and acute lymphoid and myeloid leukemias" Leukemia. Jul. 28, 2005; 19: 1567-72.

Bacher, et al. "Prognostic relevance of FLT3-TKD mutations in AML: the combination matters—an analysis of 3082 patients" Blood. Mar. 1, 2008;111:2527-2537.

Bains, et al. "FLT3 and NPM1 mutations in myelodysplastic syndromes: Frequency and potential value for predicting progression to acute myeloid leukemia" American Journal of Clinical Pathology. Jan. 2011; 135:62-69.

Bergers, et al. "Tumorigenesis and the Angiogenic Switch" Nature Reviews Cancer, vol. 3, Jun. 2003, 401-410.

Bhamidipati, et al. FLT3 mutations in myelodysplastic syndromes(MDS) and chronic myelomonocytic leukemia (CMML). 2012. Journal of Clinical Oncology. Suppl; abstract 6597.

Borthakur, et al. "Phase I study of sorafenib in patients with refractory or relapsed acute leukemias. Haematologica" Jan. 2011; 96: 62-8. Epub Oct. 15, 2010.

Carter, et al. "Inhibition of drug-resistant mutants of ABL, KIT, and EGF receptor kinases" Proc. Natl. Acad. Sci. USA.2005; 102:11011-11016.

Cheson, et al. "Revised Recommendations of the International Working Group for Diagnosis, Standardization of Response Criteria, Treatment Outcomes, and Reporting Standards for Therapeutic Trials in Acute Myeloid Leukemia" J Clin Oncol. Dec. 15, 2003; 21: 4642-4649.

Cortes, et al. "A phase II open-label, AC220 monotherapy efficacy study in patients with refractory/relapsed FLT3-ITD positive acute myeloid leukemia: updated interim results" Blood (ASH Annual Meeting Abstracts) Dec. 2011.

Cortes, et al. "AC220, a potent, selective, second generation FLT3 receptor tyrosine kinase (RTK) inhibitor, in a first-in-human (FIH) phase I AML study" Blood (ASH Annual Meeting Abstracts) Nov. 2009.

Dicker, et al. "Trisomy 13 is strongly associated with AML1/RUNX1 mutations and increased FLT3 expression in acute myeloid leukemia," Blood. 2007;110:1308-1316.

Drexler, et al. Abstract Only: "Expression of FLT3 receptor and response to FLT3 ligand by leukemic cells" Leukemia. 1996; 10:588-599.

European Patent Office, European Search Report for EP13869984.8 dated Jul. 25, 2016, 7 pp.

European Patent Office, Communication pursuant to Article 94(3) EPC for EP13869984.8 dated May 11, 2017, 5 pp.

European Patent Office, Notice of Opposition to a European Patent (EP13869984.8) dated Mar. 7, 2018, 20 pp.

Fabian, et al. "A small molecule-kinases interaction map for clinical kinase inhibitors" Nat Biotechnol. 2005; 23:329-336.

Fathi, Amir T. "Emergence of crenolanib for FLT3-mutant AML" Blood, Nov. 21, 2013, vol. 122, No. 22.

Galanis, et al. "Crenolanib is a potent inhibitor of FLT3 with activity against resistance-conferring point mutants" Blood, Jan. 2, 2014, vol. 123, No. 1.

Galanis, et al. "Crenolanib is a Highly Potent, Selective, FLT3 TKI with Activity Against D835 Mutation" (Abstract Only) Blood 2012, 120:1341.

Gao, et al. "Combination of Crenolanib with Soragenib Produces Synergistic Pro-Apoptotic Effects in FLT3-ITD-Inhibitor-Resistant Acute Myelogenous Leukemias with FLT3 Mutations" (Abstract Only) Blood, vol. 120, No. 21 3591, published online Oct. 26, 2015, 3 pp.

Gilliland, et al. "The roles of FLT3 in hematopoiesis and leukemia" Blood. 2002; 100:1532-1542.

Griswold, et al. "Effects of MLN518, A Dual FLT3 and KIT Inhibitor, on Normal and Malignant Hematopoiesis" Blood. Nov. 2004; 104 (9): 2912-2918.

Hitoshi, et al. "Prognostic implication of FLT3 and N-RAS gene mutations in acute myeloid leukemia" Blood, vol. 93, No. 9, May 1, 1999, pp. 3074-3080.

Karaman, et al. "A quantitative analysis of kinase inhibitor selectivity" Nat Biotechnol.2008; 26:127-132.

Kindler, et al. "FLT3 as a therapeutic target in AML: still challenging after all these years" Blood. 2010; 116:5089-102.

Kiyoi, et al. "Internal Tandem duplication of the FLT3 gene is a novel modality of elongation mutation which causes constitutive activation of the product" Leukemia.1998; 12:1333-1337.

Kiyoi, et al. "Internal tandem duplication of FLT3 associated with leukocytosis in acute promyelocytic leukemia. Leukemia Study Group of the Ministry of Health and Welfare (Kohseisho)" Leukemia. 1997; 11:1447-1452.

Kiyoi, et al. "Prognostic implication of FLT3 and N-RAS gene mutations in acute myeloid leukemia" Blood. 1999; 93:3074-3080.

Korean Intellectual Property Office, International Search Report and Written Opinion for PCT/US2013/064821 dated Dec. 26, 2013, 5 pp.

Kottaridis, et al. "The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials" Blood. 2001; 98:1752-1759.

Levis, et al. "A FLT3 tyrosine kinase inhibitor is selectively cytotoxic to acute myeloid leukemia blasts harboring FLT3 internal tandem duplication mutations" Blood. Aug. 1, 2001; 98(3): 885-887.

Levis, et al. "Small Molecule FLT3 Tyrosine Kinase Inhibitors" Current Pharmaceutical Design. 2004, 10, 1183-1193.

Lewis, et al. "Phase I Study of the Safety, Tolerability, and Pharmacokinetics of Oral CP-868,596, a Highly Specific Platelet-Derived Growth Factor Receptor Tyrosine Kinase Inhibitor in Patients With Advanced Cancers" J Clin Oncol. Nov. 1, 2009; 27(31) p. 5262-5269.

Liu, et al. "Rational design of inhibitors that bind to inactive kinase conformations" Nature Chem. Biol. 2006; 2:358-354.

Manley, et al. "Advances in the structural biology, design and clinical development of Bcr-Abl kinase inhibitors for the treatment of chronic myeloid leukaemia" Biochim. Biophis. Acta. 2005;1754:3-13.

Mead, et al. "FLT3 tyrosine kinase domain mutations are biologically distinct from and have a significantly more favorable prognosis than FLT3 internal tandem duplications in patients with acute myeloid leukemia" Blood. Apr. 24, 2007; 110: 1262.

Michael, et al. "Phase Ib study of CP-868,596, a PDGFR inhibitor, combined with docetaxel with or without axitinib, VEGFR inhibitor" British Journal of Cancer (published online Oct. 19, 2010) 103, 1554-1561.

Muralidhara, et al. "Crenolanib, a novel type I, mutant-specific inhibitor of class III receptor tyrosine kinases, preferentially binds to phosphorylated kinases" Cancer Research. 2012; 72 (8 Supplement): 3683 and Poster.

Murata, et al. "Selective cytotoxic mechanism of GTP-14564, a novel tyrosine kinase inhibitor in leukemia cells expressing a constitutively active Fms-like tyrosine kinase 3 (FLT3)" J Biol Chem. 2003; 278 (35): 32892-32898 [Epub Jun. 18, 2003].

(56) References Cited

OTHER PUBLICATIONS

Nakao, et al. Abstract Only: "Internal tandem duplication of the FLT3 gene found in acute myeloid leukemia. Leukemia" 1996; 10:1911-1918.
O'Farrell, et al. "SU11248 is a novel FLT3 tyrosine kinase inhibitor with potent activity in vitro and in vivo" Blood. May 2003; 101(9): 3597-3605.
Overland, et al. "Ectopic expression of Flt3 kinase inhibits proliferation and promotes cell death in different human cancer cell lines" Cell Biol Toxicol (published online Mar. 16, 2012).
Raica, et al. "Platelet-Derived Growth Factor (PDGF)/PDGF Receptors (PDGFR) Axis as Target for Antitumor and Antiangiogenic Therapy" Pharmaceuticals (published Mar. 11, 2010), 572-599.
Schnittger, et al. "Analysis of FLT3 length mutations in 1003 patients with acute myeloid leukemia: correlation to cytogenetics, FAB subtype, and prognosis in the AMLCG study and usefulness as a marker for the detection of minimal residual disease" Blood. 2002; 100:59-66.
Sclenk, et al. "Mutations and Treatment Outcome in Cytogenetically Normal Acute Myeloid Leukemia" NEJM. May 1, 2008; 358: 1909.
Small, Donald "FLT3 mutations: biology and treatment" Hematology Am Soc Hematol Educ Program. 2006: 178-84.
Smith, et al. "Crenolanib is a selective type I plan-FLT3 inhibitor" PNAS, Apr. 8, 2014, vol. 111, No. 14, 5319-5324.
Smith, et al. "Single agent CEP-701, a novel FLT3 inhibitor, shows biologic and clinical activity in patients with relapsed or refractory acute myeloid leukemia" Blood. May 2004; 103: 3669-3676.
Smith, et al. Abstract Only "Crenolanib (CP-868,596) Is a Potent and Selective Type I FLT3 Inhibitor That Retains Activity Against AC220 Resistance-Causing FLT3 Kinase Domain Mutants" Blood 2012.
Smith, Catherine, "Oral Presentation ASH 2012, Dec. 9, 2012 of Crenolanib (CP-868,596) Is a Potent and Selective Type I FLT3 Inhibitor That Retains Activity Against AC220 Resistance-Causing FLT3 Kinase Domain Mutants"—21 pp.
Sporn, et al. "Proliferative Diseases" Am J Med. Jun. 1981;70)6):1231-5.
Stirewalt, et al. "The role of FLT3 in haematopoietic malignancies" Nature Reviews Cancer. 2003;3:650-665.
Stone, et al. "PKC-412 FLT3 inhibitor therapy in AML: results of a phase II trials" Ann Hematol. 2004; 83 Suppl 1: S89-90.
Taeger, et al. "Targeting FGFR/PDGFR/VEGFR Impairs Tumor Growth, Angiogenesis, and Metastasis by Effects on Tumor Cells, Endothelial Cells, and Pericytes in Pancreatic Cancer" Molecular Cancer Therapeutics, (published online Sep. 1, 2011) 2157-2167.
Takahashi, Shinichiro "Downstream molecular pathways of FLT3 in the pathogenesis of acute myeloid leukemia: biology and therapeutic implications" Journal of Hematology & Oncology, 2011, 4:13.
Thiede, et al. "Analysis of FLT3-activating mutations in 979 patients with acute myelogenous leukemia: association with FAB subtypes and identification of subgroups with poor prognosis" Blood. 2002; 99:4326-4335.
Tse, et al. Inhibition of FLT3-mediated transformation by use of a tyrosine kinase inhibitor Leukemia. Jul. 2001; 15(7): 1001-1010.
U.S. National Library of Medicine, ClinicalTrials.gov archive, History of Changes for Study: NCT01522469, Phase II Study of Crenolanib in Subjects With Relapsed/Refractory AML With FLT3 Activating Mutations, Jan. 30, 2012, 6 pp.
U.S. National Library of Medicine, ClinicalTrials.gov (NCT01522469) first received Jan. 30, 2012, 3 pp.
U.S. National Library of Medicine, ClinicalTrials.gov (NCT01657682), A Phase II Study of Crenolanib in Relapsed/Refractory Acute Myeloid Leukemia Patients With FLT3 Activating Mutations, first received Aug. 6, 2012.
U.S. National Library of Medicine, ClinicalTrials.gov (NCT02283177), A Safety and Tolerability Study of Crenolanib in Combination With Chemotherapy in Newly Diagnosed Acute Myeloid Leukemia Patients With FLT3 Mutations, first received Nov. 5, 2014.
U.S. National Library of Medicine, ClinicalTrials.gov (NCT02400281), Study of Crenolanib Combined With Chemotheraphy in FLT3-mutated Acute Myeloid Leukemia Patients, first received Mar. 27, 2015.
Wan, et al. "Mechanism of activation of the RAF-ERK signaling pathway by oncogenic mutations of B-RAF" Cell. 2004;116:855-867.
Wikepedia, "Quizartinib", https://en.wikipedia.org/w/index.php?title=Quizartinib&oldid=528594824, Mar. 12, 2018, 2 pp.
WHO Drug Information, "International Nonproprietary Names for Pharmaceutical Substances (INN)" vol. 26, No. 1, 2012, 52 pp.
Yamamoto, et al. "Activating mutation of D835 within the activation loop of FLT3 in human hematologic malignancies" Blood. 2001; 97:2434-2439.
Yee, et al. "SU5416 and SU5614 inhibit kinase activity of wild-type and mutant FLT3 receptor tyrosine kinase" Blood. Oct. 2002; 100(8): 2941-2949.
Zhang, et al. "Targeting cancer with small molecule kinase inhibitors. Nature Reviews Cancer" 2009; 9:28-39.
Zhang, et al. "Reversal of Acquired Drug Resistance in FLT3-Mutated Acute Myeloid Leukemia Cells via Distinct Drug Combination Strategies" (published online Mar. 11, 2014) Clinical Cancer Research.
Zimmerman, et al. "Crenolanib is active against models of drug-resistant FLT3-ITD-positive acute myeloid leukemia", Blood, Nov. 21, 2013, vol. 122, No. 22.
European Patent Office, European Search Report for EP Appl. No. 1786388.6 dated Apr. 25, 2019, 13 pp.
Galanis, et al. "Abstract 3660: Crenolanib: A next generation FLT3 Inhibitor" DOI: 10.1158/1538-7445 AM2012-3660, Published Apr. 15, 2012, Cancer Research, vol. 72, Issue 8 Supplement, Abstract Only.
Intellectual Property Office of Singapore, Search Report for Singapore Patent Application No. 10201705611P dated Mar. 5, 2019, 3 pp.
Randhawa, et al. "Results of a Phase II Study of Crenolanib in Relapsed/Refractory Acute Myeloid Leukemia Patients with Activating FLT3 Mutations" Abstract Only, Blood, vol. 124, Issue 21 Blood Journal, Dec. 4, 2014, XP055570030.
Wang, et al. "Safety Study of Crenolanib, a Type I FLT3 Inhibitor, with Cytarabine/Daunorubicin or Cytarabine/Idarubicin Induction and High-Does Cytarabine Consolidation in Newly Diagnosed FLT3+ AML" EHA Learning Center, Jun. 10, 2016; 133174 Abstract Only.
Daiichi-Sankyo, "Daiichi Sankyo Announces Outcome of FDA Oncologic Drugs Advisory Committee Meeting to Review FLT3 Inhibitor Quizartinib for the Treatment of Patients with Relapsed/Refractory FLT3-ITD AML" https://www.daiichisankyo.com/media_investors/media_relations/press_releases/detail/007017.html, Nov. 2019, 3 pp.
European Medicines Agency "Refusal of the marketing authorisation for Vanflyta (quizartinib)" Oct. 18, 2019, EMA/559309/2019, 2 pp.
Ledford, Heidi "4 Ways to Fix the Clinical Trial" Nature, vol. 477, Sep. 29, 2011, pp. 526-528.
Levis, et al. "Plasma inhibitory activity (PIA): a pharmacodynamic assay reveals insights into the basis for cytotoxic response to FLT3 inhibitors" Blood, Nov. 15, 2006, vol. 108, No. 10 pp. 3477-3843.
Mak, et al. "Lost in translation: animal models and clinical trials in cancer treatment" Am J Trans Res 2014:6(2) 114-118.
Rolig, et al. "Addition of sorafenib versus placebo to standard therapy in patients aged 60 years or younger with newly diagnosed acute myeloid leukaemia (SORAML): a multicentre, phase 2, randomised controlled trial" Published online Nov. 5, 2015, Lancet Oncol 2015; 16:1691-99.
Sexauer, et al. "Terminal myeloid differentiation in vivo is induced by FLT3 inhibition in FLT3/ITDAML" Blood, Nov. 15, 2012, vol. 120, No. 20, 4205-4214.

ation of U.S. patent application Ser. No. 15/195,297, filed
CRENOLANIB FOR TREATING FLT3 MUTATED PROLIFERATIVE DISORDERS

CROSS-REFERENCE TO RELATED APPLICATIONS

This application is a continuation of U.S. patent application Ser. No. 15/715,274, filed Sep. 26, 2017, now U.S. Pat. No. 10,213,423, issued Feb. 26, 2019, which is a continuJun. 28, 2016, now U.S. Pat. No. 9,801,870 issued Oct. 31, 2017, which is a continuation of U.S. patent application Ser. No. 14/703,500, filed May 4, 2015, now U.S. Pat. No. 9,393,240 issued Jun. 19, 2016, which is a continuation of U.S. patent application Ser. No. 14/053,011, filed Oct. 14, 2013, now U.S. Pat. No. 9,101,624 issued Aug. 11, 2015, which claims priority to U.S. Provisional Application Ser. No. 61/749,695, filed Jan. 7, 2013, the entire contents of which are incorporated herein by reference.

TECHNICAL FIELD OF THE INVENTION

The present invention relates to the use of crenolanib, in a pharmaceutically acceptable salt form for the treatment of FLT3 mutated proliferative disorder(s) driven by constitutively activated mutant FLT3, and to a method of treatment of warm-blooded animals, preferably humans, in which a therapeutically effective dose of crenolanib is administered to a subject suffering from said disease or condition.

STATEMENT OF FEDERALLY FUNDED RESEARCH

Not applicable.

INCORPORATION-BY-REFERENCE OF MATERIALS FILED ON COMPACT DISC

Not applicable.

BACKGROUND OF THE INVENTION

Without limiting the scope of the invention, its background is described in connection with FLT3 tyrosine kinase.

The FMS-like tyrosine kinase 3 (FLT3) gene encodes a membrane bound receptor tyrosine kinase that affects hematopoiesis leading to hematological disorders and malignancies. See Drexler, H G et al. Expression of FLT3 receptor and response to FLT3 ligand by leukemic cells. Leukemia. 1996; 10:588-599; Gilliland, D G and J D Griffin. The roles of FLT3 in hematopoiesis and leukemia. Blood. 2002; 100:1532-1542; Stirewalt, D L and J P Radich. The role of FLT3 in hematopoietic malignancies. Nat Rev Cancer. 2003; 3:650-665. Activation of FLT3 receptor tyrosine kinases is initiated through the binding of the FLT3 ligand (FLT3-L) to the FLT3 receptor, also known as Stem cell tyrosine kinase-1 (STK-1) and fetal liver kinase-2 (flk-2), which is expressed on hematopoietic progenitor and stem cells.

FLT3 is one of the most frequently mutated genes in hematological malignancies, present in approximately 30% of adult acute myeloid leukemias (AML). See Nakao M, S Yokota and T Iwai. Internal tandem duplication of the FLT3 gene found in acute myeloid leukemia. Leukemia. 1996; 10:1911-1918; H Kiyoi, M Towatari and S Yokota. Internal Tandem duplication of the FLT3 gene is a novel modality of elongation mutation, which causes constitutive activation of the product. Leukemia. 1998; 12:1333-1337; P D Kottaridis, R E Gale, et al. The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials. Blood. 2001; 98:1742-1759; Yamamoto Y, Kiyoi H, Nakano Y. Activating mutation of D835 within the activation loop of FLT3 in human hematologic malignancies. Blood. 2001; 97:2434-2439; Thiede C, C Steudel, Mohr B. Analysis of FLT3-activating mutations in 979 patients with acute myelogenous leukemia: association with FAB subtypes and identification of subgroups with poor prognosis. Blood. 2002; 99:4326-4335.

The most common FLT3 mutations are internal tandem duplications (ITDs) that lead to in-frame insertions within the juxtamembrane domain of the FLT3 receptor. FLT3-ITD mutations have been reported in 15-35% of adult AML patients. See Nakao M, S Yokota and T Iwai. Internal tandem duplication of the FLT3 gene found in acute myeloid leukemia. Leukemia. 1996; 10:1911-1918; H Kiyoi, M Towatari and S Yokota. Internal Tandem duplication of the FLT3 gene is a novel modality of elongation mutation, which causes constitutive activation of the product. Leukemia. 1998; 12:1333-1337; H Kiyoi, T Naoe and S Yokota. Internal tandem duplication of FLT3 associated with leukocytosis in acute promyelocytic leukemia. Leukemia Study Group of the Ministry of Health and Welfare (Kohseisho). Leukemia. 1997; 11:1447-1452; S Schnittger, C Schoch and M Duga. Analysis of FLT3 length mutations in 1003 patients with acute myeloid leukemia: correlation to cytogenetics, FAB subtype, and prognosis in the AMLCG study and usefulness as a marker for the detection of minimal residual disease. Blood. 2002; 100:59-66. A FLT3-ITD mutation is an independent predictor of poor patient prognosis and is associated with increased relapse risk after standard chemotherapy, and decreased disease free and overall survival. See FM Abu-Duhier, Goodeve A C, Wilson G A, et al. FLT3 internal tandem duplication mutations in adult acute myeloid leukemia define a high risk group. British Journal of Haematology. 2000; 111:190-195; H Kiyoi, T Naoe, Y Nakano, et al. Prognostic implication of FLT3 and N-RAS gene mutations in acute myeloid leukemia. Blood. 1999; 93:3074-3080.

Less frequent are FLT3 point mutations that arise in the activation loop of the FLT3 receptor. The most commonly affected codon is aspartate 835 (D835). Nucleotide substitutions of the D835 residue occur in approximately 5-10% of adult AML patients. See DL Stirewalt and JP Radich. The role of FLT3 in haematopoietic malignancies. Nature Reviews Cancer. 2003; 3:650-665; Y Yamamoto, H Kiyoi and Y Nakano, et al. Activating mutation of D835 within the activation loop of FLT3 in human hematologic malignancies. Blood. 2001; 97:2434-2439; C Thiede, Steudal C, Mohr B, et al. A nalysis of FLT3-activating mutations in 979 patients with acute myelogenous leukemia: association with FAB subtypes and identification of subgroups with poor prognosis. Blood. 2002; 99:4326-4335; U Bacher, Haferlach C, W Kern, et al. Prognostic relevance of FLT3-TKD mutations in AML: the combination matters—an analysis of 3082 patients. Blood. 2008; 111:2527-2537.

The heightened frequency of constitutively activated mutant FLT3 in adult AML has made the FLT3 gene a highly attractive drug target in this tumor type. Several FLT3 inhibitors with varying degrees of potency and selectivity for the target have been or are currently being investigated and examined in AML patients. See T Kindler, Lipka D B, and Fischer T. FLT3 as a therapeutic target in AML: still challenging after all these years. Blood. 2010; 116:5089-102.

FLT3 inhibitors known in the art include Lestaurtinib (also known as CEP 701, formerly KT-555, Kyowa Hakko, licensed to Cephalon); CHIR-258 (Chiron Corp.); EB10 and IMC-EB10 (ImClone Systems Inc.); Midostaurin (also known as PKC412, Novartis AG); Tandutinib (also known as MLN-518, formerly CT53518, COR Therapeutics Inc., licensed to Millennium Pharmaceuticals Inc.); Sunitinib (also known as SU11248, Pfizer USA); Quizartinib (also known as AC220, Ambit Biosciences); XL 999 (Exelixis USA, licensed to Symphony Evolution, Inc.); GTP 14564 (Merck Biosciences UK); AG1295 and AG1296; CEP-5214 and CEP-7055 (Cephalon). The following PCT International Application and U.S. patent application publications disclose additional kinase modulators, including modulators of FLT3: WO 2002032861, WO 2002092599, WO 2003035009, WO 2003024931, WO 2003037347, WO 2003057690, WO 2003099771, WO 2004005281, WO 2004016597, WO 2004018419, WO 2004039782, WO 2004043389, WO 2004046120, WO 2004058749, WO 2004058749, WO 2003024969 and U.S. Patent Application No. 20040049032. See also Levis M, KF Tse, et al. 2001 "A FLT3 tyrosine kinase inhibitor is selectively cytotoxic to acute myeloid leukemia blasts harboring FLT3 internal tandem duplication mutations." Blood 98(3): 885-887; Tse K F, et al., Inhibition of FLT3-mediated transformation by use of a tyrosine kinase inhibitor. Leukemia. July 2001; 15 (7): 1001-1010; Smith, B. Douglas et al., Single agent CEP-701, a novel FLT3 inhibitor, shows biologic and clinical activity in patients with relapsed or refractory acute myeloid leukemia Blood, May 2004; 103: 3669-3676; Griswold, Ian J. et al., Effects of MLN518, A Dual FLT3 and KIT Inhibitor, on Normal and Malignant Hematopoiesis. Blood, November 2004; 104 (9): 2912-2918 [Epub ahead of print July 8]; Yee, Kevin W. H. et al., SU5416 and SU5614 inhibit kinase activity of wild-type and mutant FLT3 receptor tyrosine kinase. Blood, October 2002; 100(8): 2941-2949. O'Farrell, Anne-Marie et al., SU11248 is a novel FLT3 tyrosine kinase inhibitor with potent activity in vitro and in vivo. Blood, May 2003; 101(9): 3597-3605; Stone, R. M et al., PKC-412 FLT3 inhibitor therapy in AML: results of a phase II trials. Ann. Hematol. 2004; 83 Suppl 1:S89-90; and Murata, K. et al., Selective cytotoxic mechanism of GTP-14564, a novel tyrosine kinase inhibitor in leukemia cells expressing a constitutively active Fms-like tyrosine kinase 3 (FLT3). J Biol Chem. Aug. 29, 2003; 278 (35): 32892-32898 [Epub 2003 Jun. 18]; Levis, Mark et al., Small Molecule FLT3 Tyrosine Kinase Inhibitors. Current Pharmaceutical Design, 2004, 10, 1183-1193.

The aforementioned inhibitors have either been or are currently being investigated in the preclinical setting, or phase I and II trials as monotherapy in relapsed AML, or in phase III combination studies in relapsed AML. Despite reports of successful inhibition of FLT3 with these compounds in preclinical studies, complete remissions have rarely been achieved in FLT3 mutant AML patients in the clinical setting. In the majority of patients, the clinical response is short-lived. Response criteria for AML clinical trials are adapted from the International Working Group for AML. See Cheson et al. Revised Recommendations of the International Working Group for Diagnosis, Standardization of Response Criteria, Treatment Outcomes, and Reporting Standards for Therapeutic Trials in Acute Myeloid Leukemia. J Clin Oncol. 2003; 21: 4642-4649. Responders are patients who obtain a Complete Response (CR), Complete Response with incomplete blood count recovery (CRi), or Partial Remission (PR). Briefly, criteria are as follows:

1. Complete Remission (CR):
    a. Peripheral blood counts:
        i. No circulating blasts
        ii. Neutrophil count ≥1.0×10$^9$/L
        iii. Platelet count ≥100×10$^9$/L
    b. Bone marrow aspirate and biopsy:
        i. ≤5% blasts
        ii. No Auer Rods
        iii. No extramedullary leukemia
2. Complete remission with incomplete blood count recovery (CRi):
    a. Peripheral blood counts:
        i. No circulating blasts
        ii. Neutrophil count ≤1.0×10$^9$/L, or
        iii. Platelet count ≤100×10$^9$/L
    b. Bone marrow aspirate and biopsy
        i. ≤5% blasts
        ii. No Auer Rods
        iii. No extramedullary leukemia
3. Partial remission:
    a. All CR criteria if abnormal before treatment except:
    b. ≥50% reduction in bone marrow blast but still >5%

To date, clinical responses to FLT3 inhibitors have been primarily limited to clearance of peripheral blood (PB) blasts, which frequently return within a matter of weeks, while bone marrow (BM) blasts remain largely unaffected. For example, treatment with sorafenib, the prior mentioned multi-kinase inhibitor with activity against mutant FLT3, while effective in clearing PB blasts, has resulted in only modest BM blast reductions. See G Borthakur et al. Phase I study of sorafenib in patients with refractory or relapsed acute leukemias. Haematologica. January 2011; 96: 62-8. BM blast percentage plays a central role in the diagnosis and classification of AML. The presence of a heightened percentage of blasts in BM is associated with significantly shorter overall survival. See Small D. FLT3 mutations: biology and treatment. Hematology Am Soc Hematol Educ Program. 2006: 178-84; HM Amin et al. Having a higher blast percentage in circulation than bone marrow: clinical implications in myelodysplastic syndrome and acute lymphoid and myeloid leukemias. Leukemia. 2005; 19: 1567-72. To effectively treat FLT3 mutated AML patients and overcome the significant unmet need in this patient population, an inhibitor that significantly depletes both PB and BM blasts, bridge high risk and heavily pretreated patients to stem cell transplant, and can help to decrease relapse rates and increase overall survival in early stage disease patients. The current invention seeks to overcome disadvantages of the prior art.

SUMMARY OF THE INVENTION

In one embodiment, the present invention includes a method for treating a FLT3 mutated proliferative disorder in a patient which comprises administering to the patient a therapeutically effective amount of crenolanib or a pharmaceutically acceptable salt thereof. In one aspect, the method may also include identifying a patient with a proliferative disorder selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the therapeutically effective amounts of crenolanib or a pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day. In another aspect, the crenolanib or a pharmaceutically acceptable salt thereof is administered at least one of continuously, intermittently, systemically, or locally. In another aspect, the mutated FLT3 is defined further as a constitutively active FLT3 mutant. In another aspect, the crenolanib or a pharmaceutically acceptable salt thereof is administered orally, intravenously, or intraperitoneally. In another aspect, the crenolanib or a pharmaceutically acceptable salt thereof is crenolanib besylate, crenolanib phosphate, crenolanib lactate, crenolanib hydrochloride, crenolanib citrate, crenolanib acetate, crenolanib toluenesulphonate and crenolanib succinate. In another aspect, the FLT3 is at least one of FLT3-ITD or FLT3-TKD. In another aspect, the therapeutically effective amount of crenolanib or a pharmaceutically acceptable salt thereof is administered up to three times or more a day for as long as the subject is in need of treatment for the proliferative disorder. In another aspect, the crenolanib or a pharmaceutically acceptable salt thereof is provided at least one of sequentially or concomitantly, with another pharmaceutical agent in a newly diagnosed proliferative disorder patient, to maintain remission of an existing patient, or a relapsed/refractory proliferative disease patient. In another aspect, the crenolanib or a pharmaceutically acceptable salt thereof is provided as a single agent or in combination with another pharmaceutical agent in a patient with a newly diagnosed proliferative disorder, to maintain remission, or a relapsed/refractory proliferative disease patient. In another aspect, the crenolanib or a pharmaceutically acceptable salt thereof is provided as a single agent or in combination with another pharmaceutical agent in a newly diagnosed proliferative disorder pediatric patient, to maintain remission, or a relapsed/refractory proliferative disorder pediatric patient. In another aspect, the patient is relapsed/refractory to other FLT3 tyrosine kinase inhibitors.

Another embodiment of the present invention includes a method for treating a patient suffering from a proliferative disease comprising: identifying the patient in need of therapy for the proliferative disease; and administering to the patient in need of such treatment a therapeutically effective amount of Crenolanib or a salt thereof, wherein the cell proliferative disorder is characterized by deregulated FLT3 receptor tyrosine kinase activity, wherein the proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In one aspect, the crenolanib or a pharmaceutically acceptable salt thereof is administered orally, intravenously, or intraperitoneally. In another aspect, the crenolanib or a pharmaceutically acceptable salt thereof is at least one of Crenolanib Besylate, Crenolanib Phosphate, Crenolanib Lactate, Crenolanib Hydrochloride, Crenolanib Citrate, Crenolanib Acetate, Crenolanib Touluenesulphonate and Crenolanib Succinate Crenolanib Besylate. In another aspect, the FLT3 is at least one of FLT3-ITD or FLT3-TKD. In another aspect, the crenolanib or a pharmaceutically acceptable salt thereof is provided at least one of sequentially or concomitantly, with another chemotherapeutic agent in a newly diagnosed proliferative disease, to maintain remission, or a relapsed/refractory proliferative disease. In another aspect, the crenolanib or a pharmaceutically acceptable salt thereof is provided as a single agent or in combination with another chemotherapeutic agent for treatment of pediatric patient with the proliferative disease. In another aspect, the crenolanib or a pharmaceutically acceptable salt thereof is provided as a single agent to at least one of post standard induction therapy, or high dose induction therapy, in newly diagnosed proliferative disease. In another aspect, the crenolanib or a pharmaceutically acceptable salt thereof is provided as a single agent in treatment of patients with the proliferative disease that is either refractory to, or has relapsed after prior treatment with a chemotherapeutic agent. In another aspect, the patient is refractory to at least one other tyrosine kinase inhibitor.

Yet another embodiment of the present invention includes a method for treating a patient suffering from leukemia comprising: obtaining a sample from the patient suspected of having a leukemia; determining from the patient sample that the patient has a deregulated FLT3 receptor tyrosine kinase; and administering to the patient in need of such treatment a therapeutically effective amount of Crenolanib or a salt thereof, wherein the leukemia is characterized by deregulated FLT3 receptor tyrosine kinase activity. In one aspect, the leukemia is selected from Hodgkin's disease, and myeloma, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML, with trilineage myelodysplasia (AMLITMDS), mixed lineage leukemia (MLL), myelodysplastic syndromes (MDSs), myeloproliferative disorders (MPD), and multiple myeloma (MM).

Yet another embodiment of the present invention includes a method for specifically inhibiting a deregulated receptor tyrosine kinase comprising: obtaining a patient sample and determining which receptor tyrosine kinases are deregulated; and administering to a mammal in need of such treatment a therapeutically effective amount of crenolanib or a salt thereof, wherein the deregulated receptor tyrosine kinase is a FLT3 receptor tyrosine kinase. In one aspect, the therapeutically effective amount of crenolanib or a salt thereof is provided in an amount that decreases patient circulating peripheral blood blast count. In another aspect, the therapeutically effective amount of crenolanib or a salt thereof is provided in an amount that decreases a patient bone marrow blast count. In another aspect, the proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the therapeutically effective amount can also be a prophylactically effective amount of crenolanib or a salt thereof and are from about 50 to 500 mg per day, 100 to 450 mg per day, 200 to 400 mg per day, 300 to 500 mg per day, 350 to 500 mg per day, or 400 to 500 mg per day. In another aspect, the crenolanib or a salt thereof is administered at least one of continuously, intermittently, systemically, or locally. In another aspect, the deregulated FLT3 is defined further as a mutated FLT3 is constitutively active. In another aspect, the crenolanib or a salt thereof is administered orally, intravenously, or intraperitoneally. In another aspect, the crenolanib or a salt thereof is at least one of Crenolanib Besylate, Crenolanib Phosphate, Crenolanib Lactate, Crenolanib Hydrochloride, Crenolanib Citrate, Crenolanib Acetate, Crenolanib Touluenesulphonate and Crenolanib Succinate Crenolanib Besylate. In another aspect, the FLT3 is at least one of FLT3-ITD or FLT3-TKD. In another aspect, the therapeutically effective amount of the crenolanib or a salt thereof is administered up to three times or more a day for as long as the subject is in need of treatment for the proliferative disease. In another aspect, the patient is provided treatment, and the method further comprises the steps of: obtaining one or more patient samples to determine the effect of the treatment, and continuing treatment until the proliferative disease is reduced or eliminated. In another aspect, the crenolanib or a salt thereof is provided at least one of sequentially or concomitantly, with another pharmaceutical agent in a newly diagnosed proliferative disease patient, to maintain remission, or a relapsed/refractory proliferative disease patient. In another aspect, the crenolanib or a salt thereof is provided as a single agent or in combination with another pharmaceutical agent in a newly diagnosed proliferative disease patient, to maintain remission, or a relapsed/refractory proliferative disease patient. In another aspect, the crenolanib or a salt thereof is provided as a single agent or in combination with another pharmaceutical agent in a newly diagnosed proliferative disease pediatric patient, to maintain remission, or a relapsed/refractory proliferative disease pediatric patient. In another aspect, the patient is relapsed/refractory to a prior tyrosine kinase inhibitor. Non-limiting examples of other FLT3 inhibitors to which the proliferative disease or disorder is resistant includes, e.g., Lestaurtinib (also known as CEP 701, Cephalon); CHIR-258 (Chiron Corp.); EB10 and IMC-EB10 (ImClone Systems Inc.); Midostaurin (also known as PKC412, Novartis AG); Tandutinib (also known as MLN-518, Millennium Pharmaceuticals Inc.); Sunitinib (also known as SU11248, Pfizer USA); Quizartinib (also known as AC220, Ambit Biosciences); XL 999 (Symphony Evolution, Inc.); GTP 14564 (Merck Biosciences UK); AG1295 and AG1296; and CEP-5214 and CEP-7055 (Cephalon).

Yet another embodiment of the present invention includes a method for treating a patient with a proliferative disease comprising: obtaining a sample from the patient; determining if the patient that has become resistant to prior tyrosine kinase inhibitors; and administering a therapeutically effective amount of Crenolanib or a salt thereof to overcome the resistance to the prior protein tyrosine kinase inhibitors. This summary of the invention does not necessarily describe all necessary features of the invention.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention comprises the use of the compounds of the present invention to treat disorders related to FLT3 kinase activity or expression in a subject, e.g., deregulated FLT3 tyrosine kinase activity.

The compound is Crenolanib (4-Piperidinamine, 1-[2-[5-[(3-methyl-3-oxetanyl) methoxy]-1H-benzimidazol-1-yl]-8-quinolinyl]) and its pharmaceutically acceptable salts, which are protein tyrosine kinase inhibitors selective for constitutively active FLT3 mutations, including FLT3 ITD and FLT3 TKD mutations. Unlike prior FLT3 inhibitors in the art, the besylate salt form of crenolanib has shown to be remarkably effective in depleting absolute circulating peripheral blood blasts and bone marrow blast percentages in heavily pretreated FLT3 mutant AML patients.

In one embodiment to this aspect, the present invention provides a method for reducing or inhibiting the kinase activity of FLT3 in a subject comprising the step of administering a compound of the present invention to the subject.

As used herein, the term "subject" refers to an animal, such as a mammal or a human, who has been the object of treatment, observation or experiment.

In other embodiments, the present invention provides therapeutic methods for treating a subject with a cell proliferative disorder driven by aberrant kinase activity of mutant FLT3. In one example, the invention provides methods for treating a cell proliferative disorder related to mutant FLT3, comprising administration of a therapeutically effective amount of a pharmaceutical composition comprising a compound of the present invention in a subject. Administration of the therapeutic agent can occur upon manifestation of symptoms characteristic of the FLT3 driven cell proliferative disorder, such that a disease or disorder treated.

As used herein, the term "therapeutically effective amount", refers to an amount of active compound or pharmaceutical salt that elicits the biological or medicinal response in a subject that is being sought by a researcher, veterinarian, medical doctor or other clinician, which includes alleviation of the symptoms of the disease or disorder being treated. Methods for determining therapeutically effective doses for pharmaceutical compositions comprising a compound of the present invention are known in the art. Techniques and compositions for making useful dosage forms using the present invention are described in one or more of the following references: Anderson, Philip 0.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); relevant portions incorporated herein by reference.

As used herein, the term "composition" refers to a product comprising the specified ingredients in the specified amounts, as well as any product, which results, directly or indirectly, from combinations of the specified ingredients in the specified amounts. In one example, the composition includes crenolanib or a pharmaceutically acceptable salt thereof in an amount sufficient for the treatment of a disease.

As used herein, the terms "FLT3 mutated proliferative disorder(s)", "disorder related to FLT3," or "disorders related to FLT3 receptor," or "disorders related to FLT3 receptor tyrosine kinase," "a deregulated FLT3 receptor tyrosine kinase disease" or "FLT3 driven cell proliferative disorder" includes diseases associated with or implicating FLT3 activity, for example, mutations leading to constitutive activation of FLT3. Examples of "FLT3 mutated proliferative disorder(s)" include disorders resulting from over stimulation of FLT3 due to mutations in FLT3, or disorders resulting from abnormally high amount of FLT3 activity due to abnormally high amount of mutations in FLT3. It is known that over-activity of FLT3 has been implicated in the pathogenesis of many diseases, including the following listed cell proliferative disorders, neoplastic disorders and cancers. Non-limiting examples of proliferative disorders for treatment with the present invention include leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy.

As used herein, the terms "proliferative disorder(s)" and "cell proliferative disorder(s)" refer to excess cell proliferation of one or more subset of cells in a multicellular organism resulting in harm (i.e. discomfort or decreased life expectancy) to the multicellular organism. Cell proliferative disorders can occur in different types of animals and humans. As used herein, "cell proliferative disorders" include neoplastic disorders.

As used herein, the term "neoplastic disorder" refers to a tumor resulting from abnormal or uncontrolled cellular growth. Examples of neoplastic disorders include, but are not limited to the following disorders, for instance: the myeloproliferative disorders, such as thrombocytopenia, essential thrombocytosis (ET), agnogenic myeloid metaplasia, myelofibrosis (MF), myelofibrosis with myeloid metaplasia (MMM), chronic idiopathic myelofibrosis (UIMF), and polycythemia vera (PV), the cytopenias, and pre-malignant myelodysplastic syndromes; cancers such as glioma cancers, lung cancers, breast cancers, colorectal cancers, prostate cancers, gastric cancers, esophageal cancers, colon cancers, pancreatic cancers, ovarian cancers, and hematological malignancies, including myelodysplasia, multiple myeloma, leukemias, and lymphomas. Examples of hematological malignancies include, for instance, leukemias, lymphomas, Hodgkin's disease, and myeloma. Also, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML, with trilineage myelodysplasia (AMLITMDS), mixed lineage leukemia (MLL), myelodysplastic syndromes (MDSs), myeloproliferative disorders (MPD), and multiple myeloma (MM). In certain embodiments, the present invention is directed at the use of crenolanib or a pharmaceutically acceptable salt thereof in an amount sufficient for the treatment of a neoplastic disorder.

In one embodiment of the present invention, the crenolanib or a pharmaceutically acceptable salt thereof is provided at least one of sequentially or concomitantly, with another chemotherapeutic agent in a newly diagnosed proliferative disease, to maintain remission, or a relapsed/refractory proliferative disease. The crenolanib or a pharmaceutically acceptable salt thereof may be provided as a single agent or in combination with another chemotherapeutic agent for treatment of pediatric patient with the proliferative disease. The crenolanib or a pharmaceutically acceptable salt thereof may also be provided as a single agent to at least one of post standard induction therapy, or high dose induction therapy, in newly diagnosed proliferative disease. The crenolanib or a pharmaceutically acceptable salt thereof may also be provided as a single agent in treatment of patients with the proliferative disease that is either refractory to, or has relapsed after prior treatment with a chemotherapeutic agent. Finally, the patient may be refractory to at least one other tyrosine kinase inhibitor prior to treatment.

In a further embodiment, the present invention can be combined with another therapy as a combination therapy for treating or inhibiting the onset of a cell proliferative disorder related to FLT3 in a subject. The combination therapy comprises the administration of a therapeutically effective amount of a compound of the present invention and one or more other anti-cell proliferation therapies including, but not limited to, chemotherapy and radiation therapy.

In an embodiment of the present invention, a compound of the present invention may be administered in combination with chemotherapy. Used herein, chemotherapy refers to a therapy involving a chemotherapeutic agent. A variety of chemotherapeutic agents may be used in combination with the present invention. By way of example only, taxane compounds, specifically docetaxel, is safely administered in combination with a compound of the present invention in a dosage of 75 mg per square meter (mg/m$^2$) of body surface area.

Chemotherapy is known to those skilled in the art. The appropriate dosage and scheme for chemotherapy will be similar to those already employed in clinical therapies wherein the chemotherapy is delivered in combination with other therapies or used alone.

In another embodiment of the present invention, compounds of the present invention may be administered in combination with radiation therapy. Used herein, "radiation therapy" refers to a therapy that comprises the exposure of a subject in need to radiation. Radiation therapy is known to those skilled in the art. The appropriate dosage and scheme for radiation therapy will be similar to those already employed in clinical therapies wherein the radiation therapy is delivered in combination with other therapies or used alone.

In another embodiment of the present invention, the compounds of the present invention may be administered in combination with a targeted therapy. As used herein, "targeted therapy" refers to a therapy targeting a particular class of proteins involved in tumor development or oncogenic signaling. For example, tyrosine kinase inhibitors against vascular endothelial growth factor have been used in treating cancers.

The present invention also includes methods that include the use of a second pharmaceutical agent in addition to compounds of the present invention, the two may be administered simultaneously or sequentially (in either order).

In one embodiment, the present invention is of the compound having formula I:

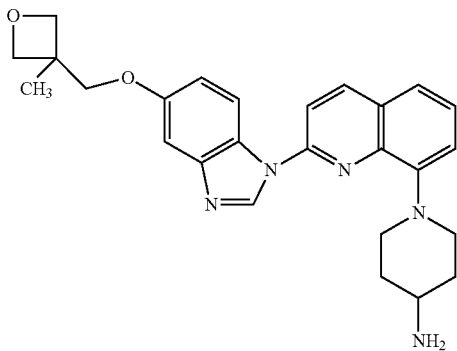 [SMILES: CC1(COc2ccc3c(c2)ncn3-c2ccc3cccc(N4CCC(N)CC4)c3n2)COC1]

or a pharmaceutically acceptable salt or solvate thereof, in a therapeutically or prophylactically effective amount against a proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. Pharmaceutically acceptable salts including hydrochloride, phosphate and lactate are prepared in a manner similar to the benzenesulfonate salt and are well known to those of moderate skill in the art.

Compounds of the present invention may be administered to a subject systemically, for example, orally, intravenously, subcutaneously, intramuscular, intradermal or parenterally. The compounds of the present invention can also be administered to a subject locally.

Compounds of the present invention may be formulated for slow-release or fast-release with the objective of maintaining contact of compounds of the present invention with targeted tissues for a desired range of time.

Compositions suitable for oral administration include solid forms, such as pills, tablets, caplets, capsules, granules, and powders, liquid forms, such as solutions, emulsions, and suspensions. Forms useful for parenteral administration include sterile solutions, emulsions and suspensions.

The daily dosage of the compounds of the present invention may be varied over a wide range from 50 to 500 mg per adult human per day. For oral administration, the compositions are preferably provided in the form of tablets containing 20 and 100 milligrams. The compounds of the present invention may be administered on a regimen up to three times or more per day. Preferably three times per day. Optimal doses to be administered may be determined by those skilled in the art, and will vary with the compound of the present invention used, the mode of administration, the time of administration, the strength of the preparation, and the details of the disease condition. Factors associated with patient characteristics, such as age, weight, and diet will call for dosage adjustments.

Preparation of the compounds of the present invention. General synthetic methods, which may be referred to for preparing the compounds of formula I are provided in U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application No. US 2005/0124599 (Pfizer, Inc.) and U.S. Pat. No. 7,183,414 (Pfizer, Inc.), relevant portions incorporated herein by reference.

Pharmaceutically acceptable salts such as hydrochloride, phosphate and lactate are prepared in a manner similar to the benzenesulfonate salt and are well known to those of moderate skill in the art. The following representative compounds of the present invention are for exemplary purposes only and are in no way meant to limit the invention, including Crenolanib as Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate.

SUMMARY OF EXAMPLES

Example 1.

Patient harbored a de novo FLT3-ITD mutation and an acquired FLT3-D835 TKD mutation. Following progression on another FLT3 inhibitor, the patient achieved a hematologic benefit categorized as a CR on crenolanib besylate therapy, and was bridged to a curative allogeneic stem cell transplant.

Example 2.

Patient harbored a de novo FLT3-ITD mutation and an acquired FLT3-D835 TKD mutation. Following progression on another FLT3 inhibitor, the patient achieved hematologic benefit categorized as a CRi on crenolanib besylate therapy, and was bridged to a curative allogeneic stem cell transplant.

Example 3.

Patient harbored acquired FLT-ITD and FLT3-D835 TKD mutations Following progression on cytotoxic chemotherapy and an autologous stem cell transplant, the patient achieved hematological benefit categorized as CRi on crenolanib besylate therapy, and was bridged to a curative allogeneic stem cell transplant.

Example 4.

Patient harbored an acquired FLT3-ITD mutation Following progression on cytotoxic chemotherapy, the patient achieved hematological benefit characterized as CRi on crenolanib besylate therapy, and was bridged to a curative allogeneic stem cell transplant.

Example 1

Effect of Crenolanib Besylate Therapy in a Relapsed/Refractory AML Patient with a de novo FLT3-ITD Mutation and Acquired FLT3-D835 TKD Mutation: CR and Bridge to Transplant.

A 34 year old, 82.28 kg male diagnosed with AML, in July 2012. At initial diagnosis, laboratory testing revealed elevated peripheral blood and bone marrow blasts. The patient was positive for a de novo FLT3-ITD mutation, categorizing him as a high risk AML patient, which is associated with poor prognosis, increased cumulative incidence of relapse and shortened overall survival.

The patient was initially treated with induction chemotherapy including a standard dose of cytarabine given as a continuous infusion for 7 days and 3 days of daunorubicin delivered intravenously. Following 1 cycle of induction therapy, the patient's bone marrow showed no evidence of AML and remission was confirmed. To maintain the clinical remission, two cycles of consolidation therapy with high dose cytarabine were completed. Approximately 1 month later, a bone marrow biopsy showed that the patient had relapsed. With no other approved standard treatment options available, the patient was enrolled on a phase I clinical trial for relapsed and refractory AML patients, where he was treated twice daily with an oral investigational FLT3 tyrosine kinase inhibitor, FLT3 tyrosine kinase inhibitor Y. Following approximately 3 months of FLT3 tyrosine kinase inhibitor Y treatment, the patient's disease progressed and he was withdrawn from the investigational study.

Further analysis showed that the patient had acquired a FLT3-TKD mutation in addition to the FLT3-ITD mutation that was present upon initial treatment. Presence of both the FLT3-ITD and FLT3-TKD mutations placed the patient in an even higher risk group. Due to the increased aggressive nature of the patient's disease, he was treated with salvage high dose cytarabine chemotherapy and hydroxyurea. Despite administration of the salvage cytotoxic regimens, there was no significant decrease in the patient's bone marrow blast counts. The patient discontinued both therapies.

To overcome resistance to prior therapy, the patient was provided single agent oral crenolanib besylate on a clinical trial for relapsed or refractory AML patients with a FLT3-D835 TKD mutation (NCT01522469). At baseline, the patient presented with 75% bone marrow blasts. The patient began treatment with 100 mg of oral crenolanib three times daily. Despite decreasing the crenolanib dose to 80 mg three times daily, after 29 days of therapy a bone marrow biopsy revealed that crenolanib overcame prior FLT3 tyrosine kinase inhibitor resistance and the patient achieved complete remission (CR). The sustained clearance of bone marrow blasts made the patient eligible for stem cell transplant (see Table 1). The patient discontinued crenolanib therapy and underwent allogeneic stem cell transplant.

Table 1 illustrates the ability of crenolanib to clear malignant leukemia in the bone marrow of Example 1, a relapsed/refractory AML patient with a de novo FLT3-ITD mutation and acquired FLT3-D835 TKD mutation, after only 29 days of therapy.

| Days on Study Drug | Bone Marrow Blast (%) |
| --- | --- |
| 0 | 75 |
| 29 | 0 |
| 57 | 1 |

Example 2

Effect of Crenolanib Besylate Therapy in a Relapsed/Refractory AML Patient with a de novo FLT3 ITD Mutation and Acquired FLT3-D835 TKD Mutation: CRi and Bridge to Transplant.

A 45 year old, 49.7 kg female diagnosed with AML in February 2012. At initial diagnosis, laboratory testing revealed an elevated bone marrow blast percentage of 65%. The patient was positive for a de novo FLT3-ITD mutation, categorizing her as a high risk AML patient, which is associated with poor prognosis, increased cumulative incidence of relapse and shortened overall survival.

The patient was initially treated with induction chemotherapy including a standard dose of cytarabine given as a continuous infusion for 5 days and 3 days of idaurubicin given intravenously. Following 1 cycle of induction therapy, the patient achieved a clinical complete remission. Laboratory tests showed a decrease in bone marrow blast percentage to 1% at week 5. To maintain the clinical remission, consolidation therapy with high dose cytarabine at 3 g/m$^2$ every 12 hours on days 1, 3, and 5 was initiated for one cycle. In preparation for a stem cell transplant, the patient underwent an observational bone marrow biopsy. At week 12 the bone marrow biopsy showed that the patient had relapsed, with a bone marrow blast percentage increase to 57%. In an effort to achieve a second remission, the patient was treated with salvage chemotherapy consisting of a combination of mitoxantrone, etoposide and cytarabine. At week 16, a bone marrow biopsy revealed that the patient had achieved a second complete remission with 3% bone marrow blasts. In preparation for a stem cell transplant, the patient underwent an observational bone marrow biopsy at week 20. The biopsy results indicated that the patient experienced a second relapse, with a bone marrow blast percentage of 30%. With no other approved standard treatment options available, the patient was enrolled on a clinical trial for relapsed and refractory AML patients, where she was treated daily with an oral investigational FLT3 tyrosine kinase inhibitor, FLT3 tyrosine kinase inhibitor X, at dose level 1. Following one treatment cycle of FLT3 tyrosine kinase inhibitor X, the patient presented with an elevated bone marrow blast percentage of 38%. Further analysis showed that the patient had acquired a FLT3-TKD mutation in addition to the FLT3-ITD mutation that was present upon initial treatment. Presence of both the FLT3-ITD and FLT3-TKD mutations placed the patient in an even higher risk group. Due to the increased aggressive nature of the patient's disease, the daily dose of FLT3 tyrosine kinase inhibitor X was increased by 100% to dose level 2. Despite the increased dose of FLT3 tyrosine kinase inhibitor X, the patient experienced an increase in bone marrow blasts to 60%. The patient discontinued the FLT3 tyrosine kinase inhibitor X investigational study.

To overcome resistance to prior therapy with FLT3 tyrosine kinase inhibitor X, the patient was provided single agent oral crenolanib besylate on a clinical trial for relapsed or refractory AML patients with a FLT3-D835 mutation (NCT01522469). At baseline, the patient presented with 91% bone marrow blasts and 4800 units/uL of absolute circulating peripheral blood blasts. The patient began treatment with 80 mg of oral crenolanib three times daily. After only 14 days of crenolanib therapy, the patient achieved complete clearance of malignant leukemic blasts in her peripheral blood. Over the course of 65 days of therapy, a bone marrow biopsy revealed that crenolanib overcame prior FLT3 tyrosine kinase inhibitor resistance and the patient achieved complete remission with incomplete blood count recovery (CRi). A decrease in bone marrow blasts to 4-5% made the patient eligible for stem cell transplant (see Tables 1 and 2). The patient discontinued crenolanib therapy and underwent allogeneic stem cell transplant.

Table 1 illustrates the ability of crenolanib to clear malignant leukemia in the peripheral blood of Example 2, a relapsed/refractory AML patient with a de novo FLT3-ITD mutation and acquired FLT3-D835 TKD mutation, after only 14 days of therapy;

| Days on Study Drug | Absolute Peripheral Blast Count (units/uL) |
|---|---|
| 1 | 4800 |
| 3 | 2747 |
| 4 | 250 |
| 7 | 49 |
| 9 | 35 |
| 14 | 0 |
| 21 | 0 |
| 28 | 0 |
| 37 | 0 |
| 38 | 0 |
| 39 | 0 |
| 40 | 0 |
| 41 | 0 |
| 42 | 0 |
| 43 | 0 |
| 45 | 0 |
| 46 | 0 |
| 47 | 0 |
| 48 | 0 |
| 49 | 0 |
| 50 | 0 |
| 51 | 0 |
| 52 | 0 |
| 69 | 0 |

| FLT3 Inhibitor | Days on Study Drug | Bone Marrow Blast (%) |
|---|---|---|
| FLT3 Inhibitor X | 0 | 30 |
| | 28 | 38 |
| | 42 | 60 |
| Crenolanib | 0 | 91 |
| | 21 | 32 |
| | 35 | 2 |
| | 65 | 4-5 |

Table 2 illustrates the ability of crenolanib to clear malignant leukemia in the bone marrow of Example 2, a relapsed/refractory AML patient with a de novo FLT3-ITD mutation and acquired FLT3-D835 TKD mulalion, for a sustained period of 65 days following immediate relapse on another investigational FLT3 inhibitor;

Example 3

Effect of Crenolanib Besylate Therapy in a Relapsed/Refractory AML Patient with acquired FLT3-ITD and FLT3-D835 TKD Mutations: CRi and Bridge to Transplant.

A 44 year old, 59.2 kg female diagnosed with AML December 2011. Following initial diagnosis the patient was treated with 7+3 induction chemotherapy, followed by consolidation therapy with 1 cycle of high dose cytarabine. Five months later the patient underwent autologous stem cell transplantation with etoposide and busulfan conditioning. There was no evidence of clinical response following transplant. Laboratory testing revealed that the patient's circulating peripheral blood blast were elevated two months later and her bone marrow blast percentage was 42% three months later. Additionally, it was discovered that the patient had acquired both a FLT3-ITD and FLT3-D835 TKD mutation. Given the in vitro FLT3 target specificity of crenolanib for both of the constitutively active mutations, the patient was initiated on the phase II crenolanib monotherapy clinical trial (NCT01522469). At baseline (Day 0), before administration of crenolanib besylate, the patient had absolute circulating peripheral blood blasts of 196 units/uL and 60-70% bone marrow blasts. The patient was treated with 100 mg of crenolanib besylate three times daily. After only 15 days of crenolanib therapy, the patient achieved complete clearance of malignant leukemic blasts in her peripheral blood. After 33 days of therapy, a bone marrow biopsy revealed that while on crenolanib therapy the patient achieved a complete remission with incomplete blood count recovery (CRi). A decrease in bone marrow blasts to 5% made the patient eligible for stem cell transplant. The patient discontinued crenolanib therapy to undergo allogeneic stem cell transplantation conditioning. The patient discontinued crenolanib therapy and underwent allogeneic stem cell transplant.

Table 3 illustrates the ability of crenolanib to clear malignant leukemia in the peripheral blood of Example 3, a heavily pretreated relapsed/refractory AML patient with acquired FLT3-ITD and FLT3-D835 TKD mutations, after only 15 days of therapy;

| Days on Study Drug | Absolute Peripheral Blast Count (units/uL) |
|---|---|
| 0 | 196 |
| 14 | 14 |
| 15 | 0 |
| 16 | 0 |
| 17 | 0 |
| 18 | 0 |
| 28 | 0 |
| 29 | 0 |
| 31 | 0 |
| 32 | 0 |
| 33 | 0 |
| 39 | 0 |
| 42 | 0 |
| 44 | 0 |
| 45 | 0 |
| 46 | 0 |
| 47 | 0 |
| 48 | 0 |
| 49 | 0 |
| 50 | 0 |
| 51 | 0 |
| 52 | 0 |

Table 4 illustrates the ability of crenolanib to clear malignant leukemia in the bone marrow of Example 3, a heavily pretreated relapsed/refractory AML patient with acquired FLT3-ITD and FLT3-D835 TKD mutations, for a sustained period of 33 days.

| Days on Study Drug | Bone Marrow Blast (%) |
|---|---|
| 0 | 60-70 |
| 27 | 10 |
| 33 | 5 |

Example 4

Effect of Crenolanib Besylate Therapy in a Relapsed/Refractory AML Patient with an acquired FLT3-ITD Mutation: CRi and Bridge to Transplant.

A 51 year old, 60.6 kg female diagnosed with FLT3-negative AML January 2012. Following initial diagnosis the patient was treated with standard 7+3 induction chemotherapy to which complete remission was achieved. The patient was then treated with 4 cycles of high dose cytarabine consolidation therapy. Laboratory testing revealed that the patient progressed on consolidation therapy. An acquired FLT3-ITD mutation was noted upon relapse and the patient was enrolled on the phase II crenolanib besylate monotherapy clinical trial (NCT01522469). At baseline (Day 0), before administration of crenolanib besylate, the patient had absolute circulating peripheral blood blasts of 198 units/uL and 76% bone marrow blasts. The patient was treated with 100 mg of crenolanib besylate three times daily. After only 15 days of crenolanib therapy, the patient achieved complete clearance of malignant leukemic blasts in her peripheral blood. After 29 days of therapy, a bone marrow biopsy revealed that while on crenolanib therapy the patient achieved a complete remission with incomplete blood count recovery (CRi). A sustained level of bone marrow leukemic blasts at 1% qualified the patient for a stem cell transplant. The patient discontinued crenolanib therapy and underwent allogeneic stem cell transplant.

Table 3 illustrates the ability of crenolanib to clear malignant leukemia in the peripheral blood of Example 4, a relapsed/refractory AML patient with an acquired FLT3-ITD mutation, after only 15 days of therapy;

| Days on Study Drug | Absolute Peripheral Blast Count (cells/uL) |
|---|---|
| 0 | 198 |
| 1 | 130 |
| 8 | 19 |
| 15 | 0 |
| 22 | 0 |
| 29 | 0 |
| 58 | 0 |

Table 4 illustrates the ability of crenolanib to clear malignant leukemia in the bone marrow of Example 4, a relapsed/refractory AML patient with an acquired FLT3-ITD mutation, after only 29 days of therapy.

| Days on Study Drug | Bone Marrow Blast (%) |
|---|---|
| 0 | 76 |
| 29 | 1 |
| 58 | 1 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Drexler, HG et al. Expression of FLT3 receptor and response to FLT3 ligand by leukemic cells. Leukemia. 1996; 10:588-599.

Gilliland, DG and JD Griffin. The roles of FLT3 in hematopoiesis and leukemia. Blood. 2002; 100:1532-1542.

Stirewalt, DL and JP Radich. The role of FLT3 in hematopoietic malignancies. Nat Rev Cancer. 2003; 3:650-665.

Nakao M, S Yokota and T Iwai. Internal tandem duplication of the FLT3 gene found in acute myeloid leukemia. Leukemia. 1996; 10:1911-1918.

H Kiyoi, M Towatari and S Yokota. Internal Tandem duplication of the FLT3 gene is a novel modality of elongation mutation which causes constitutive activation of the product. Leukemia. 1998; 12:1333-1337.

PD Kottaridis, RE Gale, et al. The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials. Blood. 2001; 98:1742-1759.

Yamamoto Y, Kiyoi H, Nakano Y. Activating mutation of D835 within the activation loop of FLT3 in human hematologic malignancies. Blood. 2001; 97:2434-2439.

Thiede C, C Steudel, Mohr B. Analysis of FLT3-activating mutations in 979 patients with acute myelogenous leukemia: association with FAB subtypes and identification of subgroups with poor prognosis. Blood. 2002; 99:4326-4335.

H Kiyoi, T Naoe and S Yokota. Internal tandem duplication of FLT3 associated with leukocytosis in acute promyelocytic leukemia. Leukemia Study Group of the Ministry of Health and Welfare (Kohseisho). Leukemia. 1997; 11:1447-1452.

S Schnittger, C Schoch and M Duga. Analysis of FLT3 length mutations in 1003 patients with acute myeloid leukemia: correlation to cytogenetics, FAB subtype, and prognosis in the AMLCG study and usefulness as a marker for the detection of minimal residual disease. Blood. 2002; 100:59-66.

FM Abu-Duhier, Goodeve AC, Wilson GA, et al. FLT3 internal tandem duplication mutations in adult acute myeloid leukemia define a high risk group. British Journal of Haematology. 2000; 111:190-195.

H Kiyoi, T Naoe, Y Nakano, et al. Prognostic implication of FLT3 and N-RAS gene mutations in acute myeloid leukemia. Blood. 1999; 93:3074-3080.

U Bacher, Haferlach C, W Kern, et al. Prognostic relevance of FLT3-TKD mutations in AML: the combination matters—an analysis of 3082 patients. Blood. 2008; 111: 2527-2537.

T Kindler, Lipka DB, and Fischer T. FLT3 as a therapeutic target in AML: still challenging after all these years. Blood. 2010; 116:5089-102.

M Levis M, KF Tse, et al. A FLT3 tyrosine kinase inhibitor is selectively cytotoxic to acute myeloid leukemia blasts harboring FLT3 internal tandem duplication mutations. Blood. 2001; 98(3): 885-887.

Tse K F, et al. Inhibition of FLT3-mediated transformation by use of a tyrosine kinase inhibitor. Leukemia. July 2001; 15 (7): 1001-1010.

Smith, B. Douglas et al. Single agent CEP-701, a novel FLT3 inhibitor, shows biologic and clinical activity in patients with relapsed or refractory acute myeloid leukemia. Blood. May 2004; 103: 3669-3676

Griswold, Ian J. et al. Effects of MLN518, A Dual FLT3 and KIT Inhibitor, on Normal and Malignant Hematopoiesis. Blood. November 2004; 104 (9): 2912-2918.

Yee, Kevin W. H. et al. SU5416 and SU5614 inhibit kinase activity of wild-type and mutant FLT3 receptor tyrosine kinase. Blood. October 2002; 100(8): 2941-2949.

O'Farrell, Anne-Marie et al. SU11248 is a novel FLT3 tyrosine kinase inhibitor with potent activity in vitro and in vivo. Blood. May 2003; 101(9): 3597-3605.

Stone, R. M et al. PKC-412 FLT3 inhibitor therapy in AML: results of a phase II trials. Ann Hematol. 2004; 83 Suppl 1:S89-90.

Murata, K. et al. Selective cytotoxic mechanism of GTP-14564, a novel tyrosine kinase inhibitor in leukemia cells expressing a constitutively active Fms-like tyrosine kinase 3 (FLT3). J Biol Chem. 2003; 278 (35): 32892-32898 [Epub 2003 Jun. 18].

Levis, Mark et al. Small Molecule FLT3 Tyrosine Kinase Inhibitors. Current Pharmaceutical Design. 2004, 10, 1183-1193.

Borthakur et al. Phase I study of sorafenib in patients with refractory or relapsed acute leukemias. Haematologica. January 2011; 96: 62-8. Epub 2010 Oct. 15.

Small D. FLT3 mutations: biology and treatment. Hematology Am Soc Hematol Educ Program. 2006: 178-84.

HM Amin et al. Having a higher blast percentage in circulation than bone marrow: clinical implications in myelodysplastic syndrome and acute lymphoid and myeloid leukemias. Leukemia. 2005; 19: 1567-72.

J Cortes et al. AC220, a potent, selective, second generation FLT3 receptor tyrosine kinase (RTK) inhibitor, in a first-in-human (FIH) phase I AML study. Blood (ASH Annual Meeting Abstracts) 2009 November J Cortes et al. A phase II open-label, AC220 monotherapy efficacy study in patients with refractory/relapsed FLT3-ITD positive acute myeloid leukemia: updated interim results. Blood (ASH Annual Meeting Abstracts) 2011 December N Lewis et al., J Clin Oncol. 2009; 27: p 5262-5269.

A Mead et al. FLT3 tyrosine kinase domain mutations are biologically distinct from and have a significantly more favorable prognosis than FLT3 internal tandem duplications in patients with acute myeloid leukemia. Blood. 2007; 110: 1262; R Schlenk et al. Mutations and Treatment Outcome in Cytogenetically Normal Acute Myeloid Leukemia. NEJM. 2008; 358: 1909.

Cheson et al. Revised Recommendations of the International Working Group for Diagnosis, Standardization of Response Criteria, Treatment Outcomes, and Reporting Standards for Therapeutic Trials in Acute Myeloid Leukemia. J Clin Oncol. 2003; 21: 4642-4649.

What is claimed is:

1. A method for treating a FLT3 mutated hematologic malignancy in a patient that comprises administering to the patient a therapeutically effective amount of crenolanib or a pharmaceutically acceptable salt thereof, wherein the FLT3 mutated hematologic malignancy is selected from at least one of a leukemia, myeloma, myeloproliferative disease, myelodysplastic syndrome, or idiopathic hypereosinophilic syndrome (HES).

2. The method of claim 1, wherein the therapeutically effective amount of crenolanib or a pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day.

3. The method of claim 1, wherein the mutated FLT3 is defined further as a constitutively active FLT3 mutant.

4. The method of claim 1, wherein the therapeutically effective amount of crenolanib or a pharmaceutically acceptable salt thereof is administered orally, intravenously, or intraperitoneally.

5. The method according to claim 1, wherein the crenolanib is crenolanib besylate, crenolanib phosphate, crenolanib lactate, crenolanib hydrochloride, crenolanib citrate, crenolanib acetate, crenolanib toluenesulphonate and crenolanib succinate.

6. The method of claim 1, wherein the FLT3 is at least one of FLT3-ITD or FLT-TKD.

7. The method of claim 1, wherein the therapeutically effective amount of crenolanib or a pharmaceutically acceptable salt thereof is at least one of: (1) administered at least one of continuously, intermittently, systemically, or locally, (2) administered up to three times or more a day for as long as the subject is in need of treatment for the FLT3 mutated hematologic malignancy; (3) sequentially or concomitantly, with another pharmaceutical agent in a newly diagnosed hematologic malignancy patient, to maintain remission, or a relapsed/refractory hematologic malignancy patient; (4) as a single agent or in combination with another pharmaceutical agent in a newly diagnosed FLT3 mutated hematologic malignancy patient, to maintain remission, or a relapsed/refractory hematologic malignancy patient; or (5) as a single agent or in combination with another pharmaceutical agent in a newly diagnosed FLT3 mutated hematologic malignancy pediatric patient, to maintain remission, or a relapsed/refractory FLT3 mutated hematologic malignancy pediatric patient.

8. The method of claim 1, wherein the patient is relapsed/refractory to other FLT3 tyrosine kinase inhibitors or another chemotherapy.

9. A method for treating a patient suffering from a FLT3 mutated hematologic malignancy comprising:
identifying the patient in need of therapy for the FLT3 mutated hematologic malignancy; and
administering to the patient in need of such treatment a therapeutically effective amount of crenolanib or a salt thereof, wherein the FLT3 mutated hematologic malignancy is characterized by deregulated FLT3 receptor tyrosine kinase activity, wherein the FLT3 mutated hematologic malignancy is selected from at least one of a leukemia, myeloma, myeloproliferative disease, myelodysplastic syndrome, idiopathic hypereosinophilic syndrome (HES).

10. The method of claim 9, wherein the crenolanib or a salt thereof is administered orally, intravenously, or intraperitoneally.

11. The method of claim 9, wherein the Crenolanib or a salt thereof is at least one of crenolanib besylate, crenolanib phosphate, crenolanib lactate, crenolanib hydrochloride, crenolanib citrate, crenolanib acetate, crenolanib touluenesulphonate and crenolanib succinate.

12. The method of claim 9, wherein the FLT3 is at least one of FLT3-ITD or FLT3-TKD.

13. The method of claim 9, wherein the therapeutically effective amount of crenolanib or a pharmaceutically acceptable salt thereof is at least one of: (1) administered at least one of continuously, intermittently, systemically, or locally, (2) administered up to three times or more a day for as long as the subject is in need of treatment for the FLT3 mutated hematologic malignancy; (3) sequentially or concomitantly, with another pharmaceutical agent in a newly diagnosed FLT3 mutated hematologic malignancy patient, to maintain remission, or a relapsed/refractory FLT3 mutated hematologic malignancy patient; (4) as a single agent or in combination with another pharmaceutical agent in a newly diagnosed FLT3 mutated hematologic malignancy patient, to maintain remission, or a relapsed/refractory hematologic malignancy patient; or (5) as a single agent or in combination with another pharmaceutical agent in a newly diagnosed FLT3 mutated hematologic malignancy pediatric patient, to maintain remission, or a relapsed/refractory hematologic malignancy pediatric patient.

14. The method of claim 9, wherein the patient is refractory to at least one other tyrosine kinase inhibitor or another chemotherapy.

15. A method for treating a patient suffering from leukemia comprising:
obtaining a sample from the patient suspected of having leukemia;
determining from the patient sample that the patient has a deregulated FLT3 receptor tyrosine kinase; and
administering to the patient in need of such treatment a therapeutically effective amount of crenolanib or a salt thereof, wherein the leukemia is characterized by deregulated FLT3 receptor tyrosine kinase activity.

16. The method of claim 15, wherein the leukemia is selected from Hodgkin's disease, and myeloma, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML, with trilineage myelodysplasia (AMLITMDS), mixed lineage leukemia (MLL), myelodysplastic syndromes (MDSs), myeloproliferative disorders (MPD), and multiple myeloma (MM).

17. A method for specifically inhibiting a deregulated receptor tyrosine kinase comprising:
obtaining a patient sample;
determining which receptor tyrosine kinases are deregulated; and
administering to a mammal in need of such treatment a therapeutically effective amount of crenolanib or a salt thereof, wherein the deregulated receptor tyrosine kinase is a FLT3 receptor tyrosine kinase sufficient to treat a FLT3 mutated hematologic malignancy, wherein the FLT3 mutated hematologic malignancy is selected from at least one of a leukemia, myeloma, myeloproliferative disease, myelodysplastic syndrome, idiopathic hypereosinophilic syndrome (HES).

18. The method of claim 17, wherein the therapeutically effective amount of crenolanib or a salt thereof is provided in an amount that decreases patient circulating peripheral blood blast count.

19. The method of claim 17, wherein the therapeutically effective amount of crenolanib or a salt thereof is provided in an amount that decreases a patient bone marrow blast count.

20. The method of claim 17, wherein the therapeutically effective amount of crenolanib or a salt thereof is also provided prophylactically at effective amounts are from about 50 to 500 mg per day, 100 to 450 mg per day, 200 to 400 mg per day, 300 to 500 mg per day, 350 to 500 mg per day, or 400 to 500 mg per day.

21. The method of claim 17, wherein the deregulated FLT3 is defined further as a mutated FLT3 is constitutively active.

22. The method of claim 17, wherein therapeutically effective amount of crenolanib or a salt thereof is administered orally, intravenously, or intraperitoneally.

23. The method of claim 17, wherein the crenolanib is at least one of crenolanib besylate, crenolanib phosphate, crenolanib lactate, crenolanib hydrochloride, crenolanib citrate, crenolanib acetate, crenolanib touluenesulphonate and crenolanib succinate.

24. The method of claim 17, wherein the FLT3 is at least one of FLT3-ITD or FLT3-TKD.

25. The method of claim 17, wherein the patient is provided treatment, and the method further comprises the steps of obtaining one or more patient samples to determine the effect of the treatment, and continuing treatment until the FLT3 mutated hematologic malignancy is reduced or eliminated.

26. The method of claim 17, wherein the therapeutically effective amount of crenolanib or a pharmaceutically acceptable salt thereof is at least one of: (1) administered at least one of continuously, intermittently, systemically, or locally, (2) administered up to three times or more a day for as long as the subject is in need of treatment for the FLT3 mutated hematologic malignancy; (3) sequentially or concomitantly, with another pharmaceutical agent in a newly diagnosed FLT3 mutated hematologic malignancy patient, to maintain remission, or a relapsed/refractory FLT3 mutated hematologic malignancy patient; (4) as a single agent or in combination with another pharmaceutical agent in a newly diagnosed FLT3 mutated hematologic malignancy patient, to maintain remission, or a relapsed/refractory FLT3 mutated hematologic malignancy patient; or (5) as a single agent or in combination with another pharmaceutical agent in a newly diagnosed FLT3 mutated hematologic malignancy pediatric patient, to maintain remission, or a relapsed/refractory FLT3 mutated hematologic malignancy pediatric patient.

27. The method of claim 17, wherein the patient is relapsed/refractory to a prior tyrosine kinase inhibitor or another chemotherapy.

28. A method for treating a patient with a hematologic malignancy comprising:
   obtaining a sample from the patient;
   determining if the patient that has become resistant to prior tyrosine kinase inhibitors or chemotherapy and has a FLT3 mutated hematologic malignancy, wherein the FLT3 mutated hematologic malignancy is selected from at least one of a leukemia, myeloma, myeloproliferative disease, myelodysplastic syndrome, or idiopathic hypereosinophilic syndrome (HES); and
   administering a therapeutically effective amount of crenolanib or a salt thereof to overcome the resistance to the prior protein tyrosine kinase inhibitors.

* * * * *